United States Patent
Leonardi

(10) Patent No.: US 11,423,120 B1
(45) Date of Patent: Aug. 23, 2022

(54) MULTI-FURCATED ALLOCATION SYSTEM

(71) Applicant: SENTRY DATA SYSTEMS, INC., Deerfield Beach, FL (US)

(72) Inventor: Travis Leonardi, Deerfield Beach, FL (US)

(73) Assignee: SENTRY DATA SYSTEMS, INC., Deerfield Beach, FL (US)

( * ) Notice: Subject to any disclaimer, the term of this patent is extended or adjusted under 35 U.S.C. 154(b) by 649 days.

(21) Appl. No.: 14/996,994

(22) Filed: Jan. 15, 2016

(51) Int. Cl.
*G06Q 10/08* (2012.01)
*G06F 19/00* (2018.01)

(52) U.S. Cl.
CPC .......... *G06F 19/326* (2013.01); *G06F 19/328* (2013.01); *G06F 19/3456* (2013.01); *G06Q 10/087* (2013.01)

(58) Field of Classification Search
CPC .. G06F 19/326; G06F 19/328; G06F 19/3456; G16H 20/10; G16H 20/60; G16H 20/70; G16H 20/90; G16H 70/40; G16H 70/60; G06Q 10/10; G06Q 40/08; G06Q 10/087
See application file for complete search history.

(56) References Cited

U.S. PATENT DOCUMENTS

| | | | | |
|---|---|---|---|---|
| 2007/0265887 A1* | 11/2007 | McLaughlin | ......... | G06F 19/328 705/4 |
| 2011/0054935 A1 | 3/2011 | Hardaway | | |
| 2014/0350952 A1* | 11/2014 | Utech | ..................... | G06Q 50/22 705/2 |
| 2015/0278924 A1 | 10/2015 | Maurer | | |
| 2016/0042147 A1* | 2/2016 | Maurer | ............... | G06F 19/3456 705/3 |
| 2016/0110519 A1* | 4/2016 | Louie | ..................... | B65B 57/10 705/2 |
| 2020/0320470 A1* | 10/2020 | Whitney | ............ | G06Q 30/0201 |

OTHER PUBLICATIONS

Sentry Data Systems, "an analysis of 340B solutions" (c) 2014 (Year: 2014).*
Sample 340B Policy & Procedures Manual, Feb. 2014, Apexus, pp. 1-18.

* cited by examiner

*Primary Examiner* — Gregory D. Moseley
(74) *Attorney, Agent, or Firm* — Loeb & Loeb LLP

(57) ABSTRACT

Example embodiments are disclosed for receiving dispensation data corresponding to dispensation of a drug associated with a covered entity, mapping a proprietary code to a standardized drug identification code for the drug, retrieving an audit record based on the standardized code, wherein the audit record identifies an order quantity of the drug ordered by the covered entity using a pricing account, allocating the dispensed quantity of the drug to the audit record up to an amount that equals but does not exceed the order quantity, applying a reorder rule to calculate when to reorder the drug, and subsequent to determining to reorder the drug in response to applying the reorder rule, communicating to a distributor an order message comprising the order quantity and the standardized code of the drug to reorder the drug using the pricing account and for causing the distributor to ship the drug.

3 Claims, 4 Drawing Sheets

Audit Record Details

← 202

| | | Allocated State: Fully Allocated ← 208 |
|---|---|---|
| Invoice No. | 7775174 | Purchased 1 |
| NDC | 51079-0525-20 | Returned 0 |
| Drug Description | ONDANSETRON HCL 8 MG 100 EA TABS | Dispensed 1 |
| CDM Code | 636Q0179D, 636QQ0162E, 636S0119E | Balance 1 = 1 |
| Invoice Line Quantity | 1 | |

Dispensations | Related Invoices

Export to Spreadsheet

Perform Trace

206 → ◄ Previous  Page [1] of 1  Next ►  Show [50] per page                                         ☐ Include Reversals 2 total rows

| ▼Date | CDM ▼Code | ▼UOIs | ▼IP / OP | ▼Medicaid | Location ▼Code | ▼Recipient | Recipient ▼DOB | Attending Physician | Attending Physician NPI |
|---|---|---|---|---|---|---|---|---|---|
| 09/11/2016 11:59:59 PM | 636Q0179D | +.1 | Outpatient | No | RCMONC | SMITH, JAN | 09/13/1951 | STAR, HAROLD | 12345 |
| 09/11/2016 11:59:59 PM | 636Q0179D | +.9 | Outpatient | No | RCCAN | WEILL, LILLY | 12/12/1959 | STAR, HAROLD | 12345 |

Totals (for all pages):                    1 dispensed           2 locations found 2 recipients found

Figure 2

MULTI-FURCATED ALLOCATION SYSTEM

BACKGROUND

Field of the Invention

The invention relates to systems and methods for linking purchases of a drug by a covered entity from a drug distributor to a dispensation of the drug by the covered entity. Among other fields and applications, the invention has utility in facilitating compliance with a drug discount program.

Description of Related Art

The U.S. federal government provides a 340B Drug Pricing Program that enables certain eligible healthcare organizations, referred to as Covered Entities (CEs), to receive discounts on drug prices. The 340B program is designed to ease the financial burden on institutions that disproportionately serve patients who are unable to pay for services they receive. CEs may be nonprofit health care organizations that meet certain Federal designations or receive funding from specific Federal programs that can purchase discounted drugs through the 340B Program. Examples of CEs include Disproportionate Share Hospitals (DSH), Sole Community Hospitals (SCH), Rural Referral Centers (RRC), Critical Access Hospitals (CAH), Children's Hospitals, Free Standing Cancer Centers, Community Health Centers (CHC), and Federally Qualified Health Centers (FQHC).

The 340B program reduces the cost of goods (typically medications) for eligible Outpatient (OP) areas of a hospital. These price reductions typically result in savings on eligible OP pharmaceutical purchases. In some instances, a CE may contract with a pharmacy (contract pharmacy or CP), which dispenses medication for the CE. Cost savings under the 340B program result from discounts given by drug manufacturers, who offer reduced drug prices in order to participate in other government programs, such as drug reimbursement under Medicaid.

To benefit from the 340B program, CEs are required to follow stringent rules and regulations. For instance, to be a compliant eligible dispensation of medication and available for replenishment of the drug under the 340B program, the following conditions must be met: (1) the medication is dispensed to an outpatient of the CE, (2) the medication is dispensed in an eligible outpatient location, (3) the medication's 11-digit National Drug Code (NDC) at dispensation matches the NDC of the medication purchased from a drug distributor, (4) an eligible physician orders the dispensation, (5) the medication is provided for an eligible service, (6) data on the dispensation is tracked accurately and is available for auditing, and (7) the medication is dispensed to a patient for whom the covered entity maintains responsibility for care.

While there are many benefits to the 340B program, complying with the regulations can be difficult for CEs and CPs.

SUMMARY

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

Example embodiments of a system, apparatus, computer readable media, and method are disclosed for receiving dispensation data corresponding to dispensation of a drug associated with a covered entity, mapping a proprietary code included in the dispensation data to a standardized drug identification code for the drug, retrieving an audit record based on the standardized code, wherein the audit record identifies an order quantity of the drug purchased by the covered entity using a pricing account, allocating the dispensed quantity of the drug to the audit record up to an amount that equals but does not exceed the order quantity, applying a reorder rule to calculate when to reorder the drug, and subsequent to determining to reorder the drug in response to applying the reorder rule, communicating to a distributor an order message comprising the order quantity and the standardized code of the drug to reorder the drug using the pricing account and for causing the distributor to ship the drug to a mailing address associated with the covered entity.

BRIEF DESCRIPTION OF THE DRAWINGS

The invention may be better understood by reference to the detailed description when considered in connection with the accompanying drawings. The components in the figures are not necessarily to scale, emphasis instead being placed upon illustrating the principles of the invention. In the figures, like reference numerals designate corresponding parts throughout the different views.

FIG. 2 depicts an audit record in accordance with example embodiments.

Figure 1:
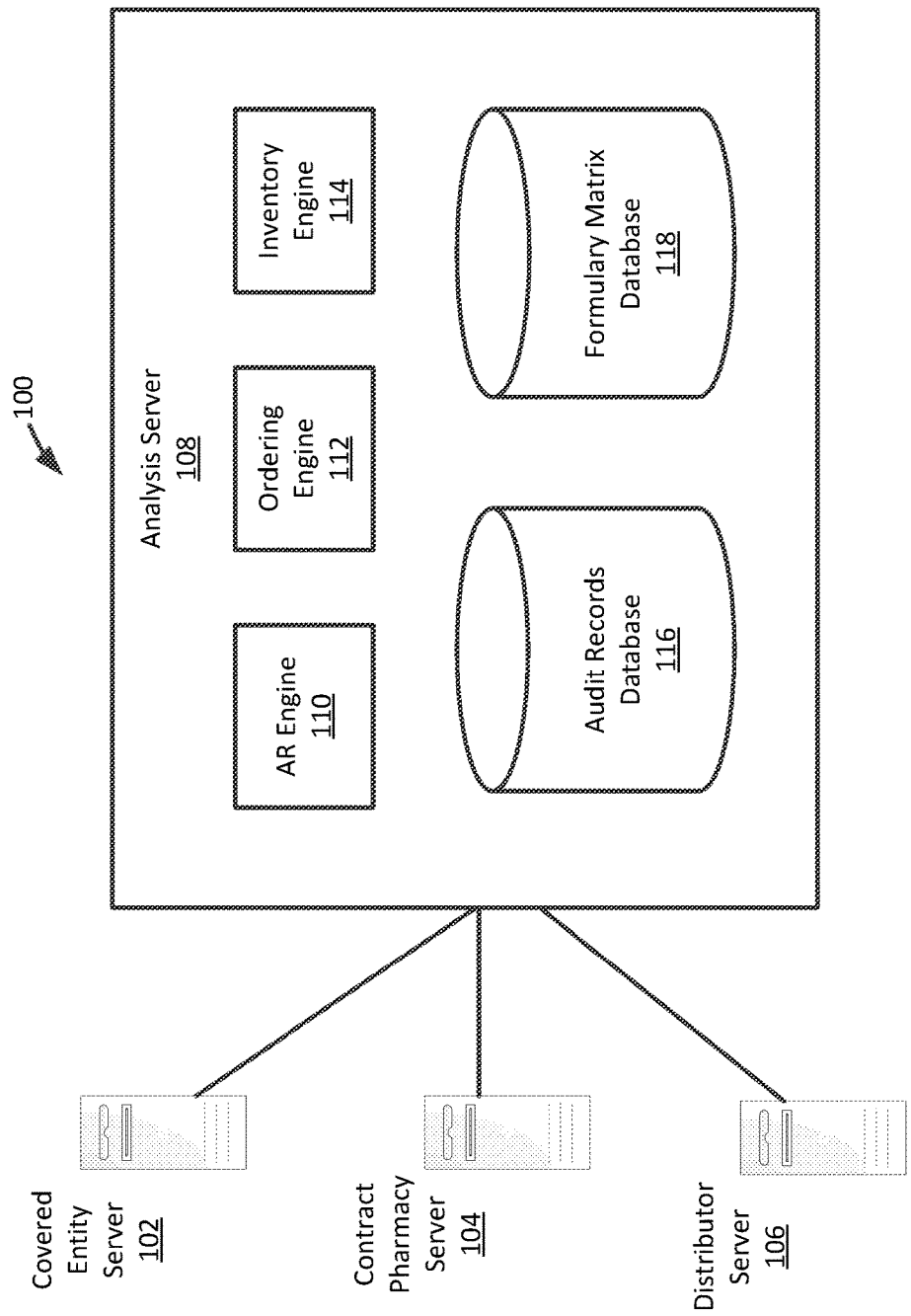
FIG. 1 illustrates a block diagram of a system in accordance with example embodiments.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

The example embodiments relate to systems and methods for linking purchases of a drug from a distributor by a covered entity, to a specific dispensation of the drug to a patient by the covered entity, and to reordering of the drug from the distributor under a drug discount program. This connection may be used to confirm that the covered entity properly reordered the drug under a drug discount program, and thus was eligible to purchase the drug from the distributor at a discounted price when replenishing its inventory, instead of at a higher wholesale price. For example, some drug discount programs, such as the 340B program, require 1-digit NDC replenishment for eligible inventory and impose strict auditing standards on participating covered entities. The example embodiments provide a manner to connect each purchase from a drug distributor by a covered entity to a specific dispensation of the drug by the covered entity.

FIG. 1 illustrates a block diagram of a system 100 in accordance with example embodiments. System 100 may include a covered entity (CE) server 102, a contract pharmacy (CP) server 104, and a distributor server 106 communicatively coupled to an analysis server 108 by a direct connection or via one or more computer networks (e.g., local area network, wide area network, wireless network, wired network, and the like, and/or some combination thereof). The CP server 104 is optional and may be omitted. For instance, the CE may handle ordering and dispensing of its drugs without assistance of a CP. In other examples, a CE may enter into a contractual agreement with a CP to dispense some or all drugs for the CE. In that scenario, the CE server 102 and/or the CP server 104 may communicate with the analysis server 108.

The CE server 102 and/or the CP server 104 may send a dispensation data feed to the analysis server 108. The dispensation data feed may include one or more dispensation messages each including information about dispensation of a drug by a CP or CE to a patient. The distributor server 106 may send an invoice data feed to the analysis server 108. The invoice data feed may include one or more discrete invoice messages each including information about sale of a drug to a CE and/or its affiliated CP. The analysis server 108 may process the dispensation and invoice data feeds to link drug purchases with drug dispensations for confirming eligibility to reorder a dispensed drug under a drug discount program.

In an example, the analysis server 108 may include an audit record (AR) engine 110, an ordering engine 112, and an inventory engine 114. Each of engines 110, 112, and 114 may be discrete pieces of hardware hard coded to perform the functions described herein. In other examples, the functions of engines 110, 112, and 114 may be implemented in software as computer readable instructions stored in memory whereby execution of the computer readable instructions by at least one processor cause the at least one computer, server, or other device, to perform the functions described herein. In yet other examples, any of the engines may implemented as discrete pieces of hardware and others may be implemented in software. In further examples, some functions performed by an engine may implemented as one or more discrete pieces of hardware and other functions may be implemented in software.

In an example, the AR engine 110 may process the dispensation and invoice data feeds to create and update audit records and determine what type of pricing account the CE may use to replenish a dispensed drug. For example, a CE may establish multiple pricing accounts with a distributor. Example types of pricing accounts are a 340B account, a Group Purchasing Organization (GPO) account, and a wholesale acquisition cost (WAC) account. The ordering engine 112 may automatically order drugs and the inventory engine 114 may track the current inventory levels of each drug.

Initially, the ordering engine 112 may receive an order request from the CE server 102 or the CP server 104. The order request may include a desired drug to order, an order quantity of the drug to order, a proprietary code of the CE assigned to the drug, a time and/or date of the order request, and the like. The order quantity may identify the quantity of a drug being ordered by a CE (e.g., 500 pills). Subsequent to receipt of the order request, the ordering engine 112 may map the proprietary code included in the dispensation data to a standardized drug identification code. A proprietary code may be a code assigned by the CE to a drug. In some instances, a CE may assign multiple proprietary codes to a drug that serve two or more purposes. For instance, a first portion of a proprietary code may be an identifier for the drug assigned by the CE and a second portion of the proprietary code may indicate what department of the CE dispensed the drug (e.g., one code for dispensation in the ER, a second code for dispensation by the oncology department). In an example, a proprietary code may be composed of multiple alphanumeric sequences. A first alphanumeric sequence may be assigned by the CE to identify a drug and a second alphanumeric sequence may identify the department that dispensed the drug. In another example, a proprietary code may also include an identifier to indicate the type of disease the drug is being used to treat. A charge description master (CDM) is an example of a proprietary code. The CDM code may be a set of proprietary codes that the ordering engine 112 maps to specific NDCs. The ordering engine 112 may access a formulary matrix stored in a formulary matrix database 118 to map each proprietary code to a particular standardized drug identification code. In an example, a formulary matrix may be a lookup table that associates each proprietary code to a particular standardized drug identification code. An NDC is an example of a standardized drug identification code. In further examples, a proprietary code may correspond to a quantity of the drug that has been dispensed, and the formulary matrix may include a rule for translating the dispensed quantity to units of issuance (UOIs, e.g., the size of a drug package when ordered from a distributor).

Subsequent to performing the mapping, the ordering engine 112 may generate an order message for communication to the distributor server 104 and to the AR engine 112. The order message may be used to order one or more drugs from the distributor and for keeping track of what drugs have been ordered. In an example, the order message may include a unique identifier for the order message, a time and/or date stamp, a standardized drug identification code (e.g., an NDC of the drug), a quantity of the drug being ordered, a CE or CP that ordered the drug, and the like. After receipt of the order message, the AR engine 110 may process the order message for creating an audit record to link purchase of a drug, to its dispensation to a patient, and to any subsequent reordering of the drug from the distributor, as described in further detail below. An audit record may be data saved in case the CE is audited for proving that the CE or CP was eligible to reorder a drug at a discounted price using a drug discount program. The audit record may be stored in an audit records database 116. The audit records database 116 may include an audit record for each drug ordered by a CE. The audit records database 116 may be a repository of audit records for multiple CEs. Each CE may or might not have a relationship with the other CEs.

FIG. 2 depicts an audit record in accordance with example embodiments. In an example, the audit record 202 may include invoice data 204, dispensation data 206, and allocation data 208. When an order message is received, the AR engine 110 may generate an audit record 202 and include at least some of the information from the order message in the record 202. For example, an audit record 202 may include a unique identifier for the order message, a time and/or date stamp of the order message, the proprietary and/or standardized code of the drug, an ordered quantity of the drug, a CE or CP that ordered the drug, and the like. The AR engine 110 may use this information to uniquely associate a drug order with a subsequent drug dispensation, and to retrieve the appropriate one of the audit records 202 from the audit records database 116 when needed for updating, such as when messages are received in the invoice and dispensation data feeds. Further, a user device may interact with the AR engine 110 to retrieve a particular audit record and display the audit record on a display screen. Examples of a user device include a computer, a tablet computer, a smart phone, a laptop computer, and the like.

Returning to FIG. 1, the distributor server 106 may also receive the order message and cause fulfillment of the order (e.g., cause physical delivery of an ordered drug to a CP or CE). In response to receipt, the distributor server 106 may process the order message to determine the standardized code (e.g., NDC) of the drug and desired quantity, and notify automated systems (e.g., robotic system(s) for packing ordered drugs into a container for shipment and for loading the container onto a vehicle for transport) and/or personnel to pack the requested drug and/or quantity for shipment to a mailing address associated with the CE that submitted the order. Also in response to receiving the order message, the distributor server 106 may communicate an invoice message to the analysis server 108 that includes invoice data 204 providing information about fulfillment of the ordered drug. In an example, invoice data 204 may identify the CE that ordered the drug, the order message identifier, a time and/or date stamp of the order message, the proprietary and/or standardized code of the drug, the order quantity of the ordered drug, a time and/or date stamp of the invoice message, an invoice number, a drug description, an invoice line quantity, an estimated delivery date for shipment of the ordered drug, and the like. In an example, an invoice number may be an alphanumeric sequence assigned by the distributor to distinguish invoices from each other. The drug description may be brief description of the ordered drug.

The AR engine 110 may process a received invoice message to update a corresponding audit record 202 with the invoice data 204 as part of linking purchase of a drug by a CE to dispensation of the drug by the CE. In an example, the AR engine 110 may process the invoice message to identify a corresponding audit record. For instance, the AR engine 110 may search the AR database 116 to find an audit record having the same information as included in the invoice message. For example, the AR engine 110 may process the invoice message to identify one or more of the order message identifier, a time and/or date stamp of the order message, the proprietary and/or standardized code of the drug, and the order quantity of the drug, and may search the database 116 for an audit record 202 having the same information. With reference to FIG. 2, the AR engine 110 may update the audit record 202 to include at least some of the received invoice data.

At some later time, the CE or CP may receive the shipment. The inventory engine 114 may determine the CE's or CP's current inventory and add the order quantity to determine a new current inventory level.

Over time, a CP or CE may dispense a drug to a patient. After or as a drug is being dispensed, the CE server 102 and/or the CP server 104 may communicate a dispensation data message to the analysis server 108. A dispensation data message may include dispensation data 206 about dispensation of a drug to a particular patient. In an example, dispensation data 206 may include one or more of the time and/or date of dispensation, a proprietary code (e.g., CDM code) of the CP or CE, a dispensation quantity indicating an amount of the drug that was dispensed, a quantity that may, for example, be translated to units of issuance (UOIs, e.g., the size of a drug package when ordered from a distributor), whether the drug was prescribed as part of inpatient or outpatient treatment, a location code, a recipient, information about the recipient (e.g., date of birth), attending physician, an NPI of the attending physician, and the like. As seen in FIG. 2, each dispensation of a particular quantity of the drug may be listed as a new row that includes information associated with a particular dispensation.

Figure 3:
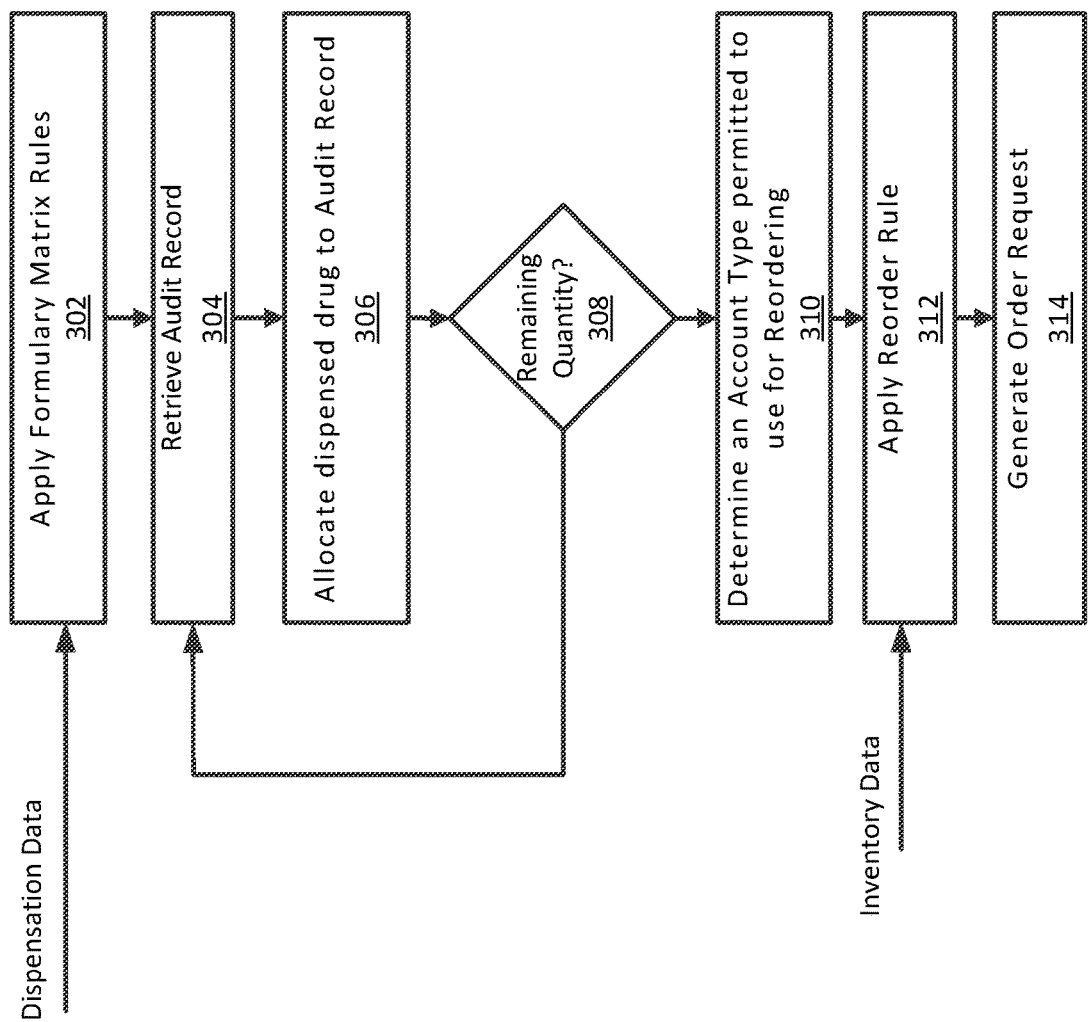
FIG. 3 depicts an example flow diagram of processing dispensation data and reordering of a drug in accordance with example embodiments.

FIG. 3 depicts an example flow diagram of processing dispensation data and reordering of a drug in accordance with example embodiments. Subsequent to when dispensation data is received, the AR engine 110 may, in block 302, receive the dispensation data and apply a formulary matrix to map a proprietary code (e.g., a CDM code) received in the dispensation data to a standardized code (e.g., an NDC). For example, the AR engine 110 may map proprietary codes (e.g., CDMs) to standard NDCs. In an example, there may be a many to many relationship between CDMs and NDCs. The AR engine 110 may also use the formulary matrix to translate quantity indicated by the dispensation data to UOI. The AR engine 110 may, in block 304, search the AR database 116 based on the CE or CP identifier and the standardized code to identify one or more audit records 202 dispensed by a particular CE or CE associated with the identifier.

In block 306, the AR engine 110 may allocate the dispensed drug to the retrieved audit record 202. Allocation may refer to associating a quantity of a drug dispensed to a patient to at least one audit record 202. In many instances, a CP or CE will order a larger quantity of a drug from a distributor than a quantity dispensed to a patient when a prescription is filled. For example, a CE may order 500 pills of a particular drug from a distributor, and may dispense no more than 30 pills to a particular patient per month. Because of this mismatch in quantities, an audit record 202 may be used to keep a running total of the quantity of a drug that has dispensed. Once the entire ordered quantity of a drug associated with a particular order has been dispensed (e.g., all 500 pills have been dispensed), the AR engine 110 may update an audit record 202 to indicate that the record has been fully allocated.

The audit record 202 may include a table listing a current allocation status of the ordered quantity of a drug on each pricing account. With reference to FIG. 2, for example, the audit record 202 may include a purchased row where a "0" indicates that a drug was not yet purchased from a distributor and a "1" indicates that a drug was initially purchased from the distributor. The AR engine 110 may update the purchased row from 0 to 1 when an invoice message is received indicating that a drug has been purchased. The audit record 202 may include a returned row where a "0" indicates that a drug was not returned by a patient and a "1" indicates that a drug was returned by a patient. The audit record 202 may include a dispensed row where a "0" indicates that the entire ordered quantity of a drug was not dispensed to one or more patients and a "1" indicates that the entire ordered quantity of a drug was completely dispensed to one or more patients. The audit record 202 may include a balance row for each pricing account and a drug is eligible to be reordered when a drug was purchased from a distributor and the entire ordered quantity was completely dispensed to a patient, but not returned.

Referring again to FIG. 3, in block 308, the AR engine 110 may determine whether there is any remainder of the dispensed quantity of the drug to be allocated to another audit record for a same type of pricing account (e.g., multiple audit records for a 340B account). If yes, then the flow diagram may return to block 304 to retrieve another audit record (e.g., associated with another 340B account) for allocating the remaining dispensed quantity to that record. For example, a CP may dispense 30 pills to a patient and an audit record associated with a 340B account may only require 20 of the 30 pills to reach 500 pills to be fully allocated (e.g., order quantity is 500 pills). The remaining 10 pills may be allocated to another audit record associated with the 340B account. Blocks 304-308 may repeat until all of the dispensed quantity has been allocated to an audit record 202. When one or more audit records 202 are fully allocated, the AR engine 110 may notify the ordering engine 112 that one or more audit records have been fully allocated. After an audit record 202 is fully allocated, the drug corresponding to that record may be reordered.

In block 310, the ordering engine 112 may determine an account type permitted to use for reordering a drug. As discussed above, a CE may establish multiple different pricing accounts with a distributor that the CE may use to purchase drugs from the distributor. Two types of accounts are a non-discounted account and a discounted account. An example of a non-discount account is a wholesale account which a CE may use to purchase drugs at a wholesale price. Examples of discounted accounts are a 340B account and a GPO account. A discounted account may be an account where some entity (e.g., a government) provides an incentive to the distributor for selling a drug to a CE at a discounted price. The U.S. Federal Government's 340B program is an example of a discount program. A GPO account is another example. The ordering engine 112 may process the retrieved audit record to determine whether the CE would be eligible to reorder a dispensed drug using a discount program. If yes, the ordering engine 112 may update the retrieved audit record to indicate which discount program(s) the CE may use when reordering. In an example, the ordering engine 112 may determine which account type to use for reordering by applying rules to determine whether the CE may reorder under one or more discount programs (e.g., whether CE may comply with 340B regulations). The ordering engine 112 may determine which of a GPO, 340B or WAC (e.g., non-discounted) account may be used when reordering a drug based on one or more of a status of patient (inpatient/outpatient), location, type of service, physician, etc.

In block 312, the ordering engine 112 may apply one or more reorder rules and process current inventory levels to determine whether to reorder a drug. In an example, the inventory engine 114 may automatically, at periodic time periods, or upon request communicate current inventory levels of the CE or CP for one or more drugs to the ordering engine 112. A reorder rule may be a set of one or more rules that the inventory engine 114 uses to determine when it is financially advantageous to reorder a particular drug. In some examples, the reorder rules may specify to automatically reorder a drug as soon as an audit record becomes fully allocated for a given pricing account. In other examples, a reorder rule may specify to reorder a drug a predetermined time after an audit record has been fully allocated. The predetermined time may permit a certain amount of time to elapse. The predetermined time may be a function of an average rate that a drug is dispensed, and the predetermined rate may vary over time as the average rate changes. The predetermined time is used attempting to handle the situation of patient returns of a drug. The CE may want to remain compliant with a drug discount program at all times, and thus the predetermined time may permit dispensation to occur to other patients, such that a dispensed quantity may be transferred from one audit record to another so that at least one of the audit accounts remains fully allocated to justify reordering.

In further examples, a reorder rule may specify to reorder a drug only after a predetermined quantity of the drug has been dispensed above the order quantity required for an audit record to be fully allocated for a given pricing type. For example, if a CE orders a drug in quantities of 100 pills and maintains at least 150 in inventory at any one time, a reorder rule may specify that at least 130 pills must be dispensed before the drug may be reordered. Dispensation of a first 100 of the 130 pills may be linked to a first audit record such that the record is fully allocated and reordering is permitted after at least 30 additional pills are allocated to a second audit record. This provides a buffer in case a patient returns 30 or fewer pills. The AR engine 110 may process the return by reallocating 30 or fewer pills from the second audit record to the first audit record so that the first audit record remains fully allocated. And hence the CE remains eligible to reorder the drug because the first audit record remained fully allocated.

In yet further examples, a reordering rule for a drug may be based on the CE's (or CP's) current inventory of the drug and a dispensation rate for the drug. For example, an inventory engine 114 of the analysis server 108 may track a current inventory level and dispensation rate of the CE or CP for a drug. The ordering engine 112 may use the current inventory level and dispensation rate as factors in determining when to reorder a drug from a distributor. For example, the ordering engine 112 may establish multiple inventory thresholds based on account type for determining when to reorder a drug based one or more of current inventory of the drug, a dispensation rate for the drug, and a discount of the drug.

To give a more concrete example, a CP may have initially purchased 100 pills of drug X from a distributor. When the CE or CP receives shipment of the drug from the distributor, the inventory engine 114 may update its current inventory levels to add 100 pills of drug X to its inventory. For example, 150 pills may be in inventory before a shipment is received and the inventory engine 114 may update the total quantity of a drug in inventory when the shipment is received (e.g., 100+150=250). In this example, the CP may order drug X in lots of 100 pills and thus drug X may be associated with three different audit records. A first audit record may have 50 of its 100 pills allocated, a second audit record may be completely unallocated, and a third audit record may be completely unallocated.

The inventory engine 114 may also monitor a historical dispensation rate on each pricing type for drug X to determine that 10 pills are dispensed per day on average. As drug X is dispensed to one or more patients, the CP server 104 may communicate a dispensation message indicating that the quantity of drug X that has been dispensed, and the analysis server 108 may update the first audit record 202 to reflect the quantity of drug X that has been dispensed until 50 additional pills have been dispensed. The AR engine 110 may then update the first audit record to indicate that it has been fully allocated. As additional pills of drug X are dispensed, the AR engine 110 may allocate up to the next 100 pills to the second audit record, and the subsequent 100 pills to the third audit record. When at least one of the three different audit records is fully allocated for a particular pricing account (e.g., audit record for a 340B account), the ordering engine 112 is eligible to reorder drug X. The ordering engine 112 may set a threshold to control when a drug is ordered based on a desired number of days-supply and a historical dispensation rate (e.g., average dispensation rate). Below is an example equation:

Threshold=Desired Number of Days Supply*Average Dispensation rate

Threshold=10 days-supply*50 pills/day=500 pills

The ordering engine 112 may vary the threshold as the historical dispensation rate changes over time.

The ordering engine 112 may also set and/or modify reorder rule thresholds based on the amount of the discount a CE receives when reordering a drug. For example, the higher the discount the higher the threshold, and the lower the discount the lower the threshold. In an example, drug X may be purchased for $500 less via a 340B account than a WAC account, whereas drug Y may be purchased for $200 less via a 340B account than a WAC account. The ordering engine 112 may establish a higher threshold for drug X than drug Y. For example, the ordering engine 112 may set the threshold for a drug as a function of its WAC price relative to its 340B price.

In an example, pills of drug X may cost $1,000 when purchased at wholesale and may cost $50 if bought using a drug discount account (e.g., a 340B account). Given the cost disparity, the ordering engine 112 may set a first threshold to more promptly reorder a drug when eligible to receive the discount, and a second threshold to less promptly order a drug when not eligible for the discount.

In a more concrete example, the ordering engine 112 may set the second threshold to based on desired number of days' supply, as set forth above. The ordering engine may set the first threshold based on a difference between a non-discounted price and a discounted price. Below is an example equation:

Threshold=Desired Inventory Level*(nondiscounted price−discounted price)/(nondiscounted Price)

In an example, this formula may set the threshold to be:

Threshold=500 units*($1,000−$50)/$1,000=475 units

In another example, this formula may set the threshold to be:

Threshold=500 units*($1,000−$500)/$1,000=250 units

Thus, a greater discount results in a higher threshold, and a lower discount results in a lower threshold. The ordering engine 112 may thus set a threshold to control when to reorder a drug based on the size of the discount.

Referring again to FIG. 3, in block 312, the ordering engine 112 may apply a reorder rule to determine when a threshold is met and generate an order request for communication to the AR engine 110 and the distributor server 106. The AR engine 110 may generate a new audit record 202 to indicate that a particular drug has been reordered using a particular pricing account and the new audit record 202 may be stored in the database 116.

The AR engine 110 may also link together an initial audit record and each subsequent audit record created when a drug was reordered using a particular pricing account. For example, a drug discount program may require that a drug be initially purchased via a non-discount account (e.g., a WAC account) to be eligible for reorder using a discount account (e.g., 340B account). A drug discount program may also require ordering of a drug via a WAC account at least once in a predetermined amount of time (e.g., once a calendar or fiscal year). To link the audit records, the AR engine 110 may assign an audit record identifier (e.g., a unique alphanumeric sequence) to each audit record when created. The AR engine 110 may link audit records together by including in a particular audit record a list of audit record identifiers for any preceding audit records and any subsequent audit records. An audit record 202 may include audit record identifiers for all connected audit records, for less than all connected audit records, or for just the immediately preceding and immediately following audit records. Thus, the AR engine 110 may create a chain between an audit record corresponding to the first time a drug was ordered through each time an audit record was generated when the drug was reordered.

Figure 4:
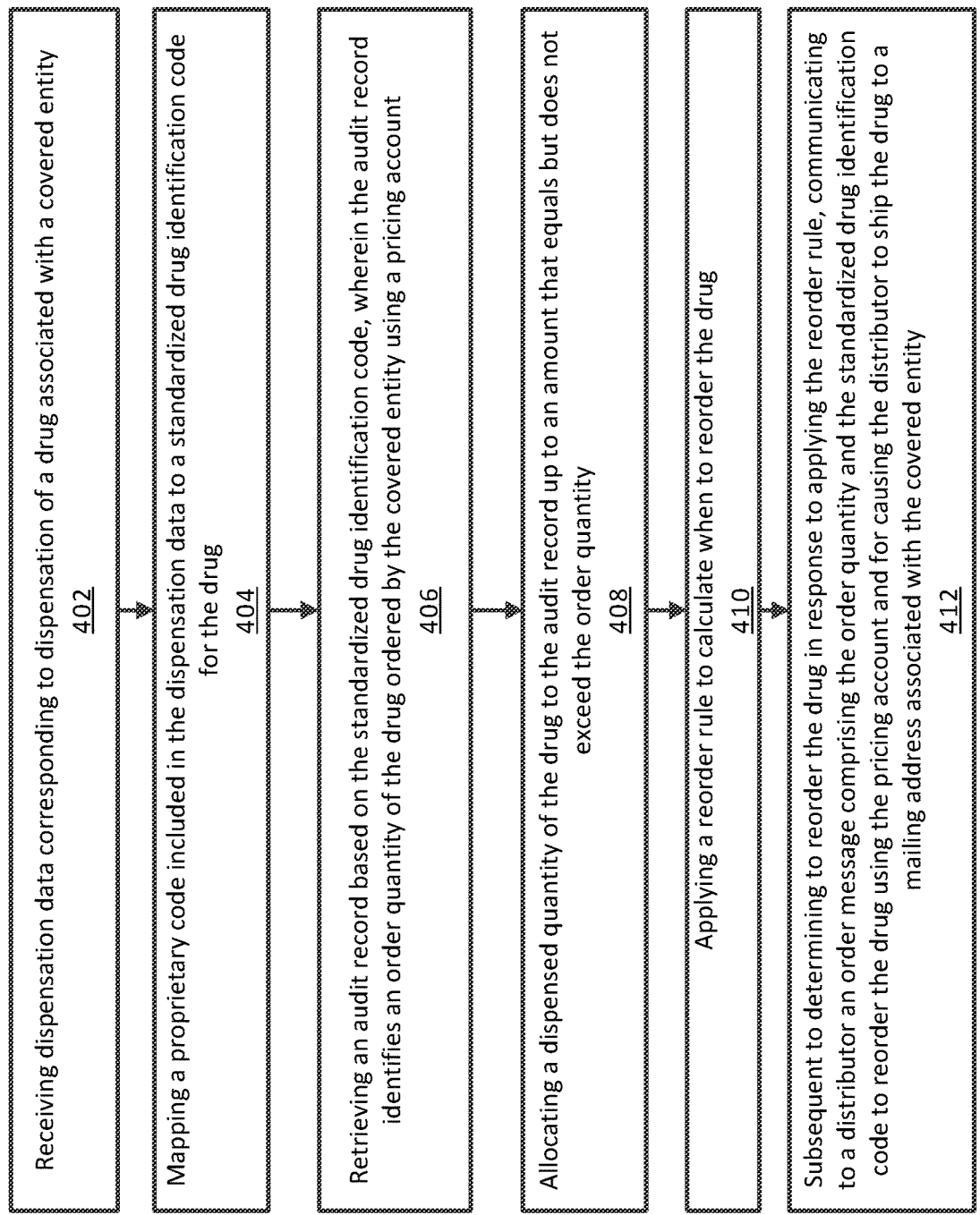
FIG. 4 illustrates a flow diagram of a method in accordance with example embodiments.

FIG. 4 illustrates a flow diagram of a method in accordance with example embodiments. The flow diagram may be implemented by a system or apparatus, such as, for example, analysis server 108. Each of the blocks shown in the flow diagram may be repeated one or more times, one or more of the blocks may be modified, and one or more of the blocks may be omitted. The method may be stored on a non-transitory computer readable medium as computer executable instructions. The computer executable instructions, when executed by at least one processor, may cause at least one computer or other device to perform the blocks as steps of a method one or more times. The flow diagram may begin at block 402.

In block 402, the method may include receiving dispensation data corresponding to dispensation of a drug associated with a covered entity, wherein the dispensation data comprises a proprietary code of the covered entity for identifying the drug and a dispensed quantity of the drug.

In block 404, the method may include mapping the proprietary code included in the dispensation data to a standardized drug identification code for the drug.

In block 406, the method may include retrieving an audit record based on the standardized drug identification code, wherein the audit record identifies a quantity of the drug ordered by the covered entity using a pricing account.

In block 408, the method may include allocating the dispensed quantity of the drug to the audit record up to an amount that equals but does not exceed the order quantity.

In block 410, the method may include applying a reorder rule to calculate when to reorder the drug.

In block 412, the method may include, subsequent to determining to reorder the drug in response to applying the reorder rule, communicating to a distributor an order message comprising the order quantity and the standardized code to reorder the drug using the pricing account and for causing the distributor to ship the drug to a mailing address associated with the covered entity.

The method of FIG. 4 may end, may repeat one or more times, or may return to any of the preceding blocks.

Advantageously, the example embodiments may facilitate a covered entity's compliance with a drug discount program, provide eligibility checks to verify drug replenishment eligibility under a drug discount program that can be tailored to the covered entity's desired level of risk, and automatically create a record should the covered entity be audited.

The example embodiments thus overcome a number of technical challenges.

For instance, conventional software does not have any mechanism for determining when to reorder drugs considering current inventory levels and compliance with a drug discount program. As described above, the ordering engine 112 may solve at least this technical challenge.

Further, mapping of a proprietary code to a standard code as described herein solves at least the technical challenge of how to identify drugs assigned proprietary codes by a CE that do not have a 1 to 1 mapping to a standardized drug identification code. In many instances, a CE may establish its own set of proprietary codes for drugs. Complicating the issue, a CE may assign the same drug distinct proprietary codes based on number of different factors (e.g., quantity dispensed, area within hospital that dispensed, etc.), and conventional software does not satisfactorily solve the challenge of how to map proprietary codes to standardized drug identification code that are CE-independent. The ordering engine 112 solves at least this technical challenge by mapping proprietary to an appropriate standard code.

The example embodiments further solve the technical challenges of conventional software that fail to provide any safeguards for maintaining compliance with regulations of a drug discount program to account for patient returns of drugs. The example embodiments may limit reordering until after a predetermined amount of time has elapsed and/or until after a predetermined amount of a drug has been dispensed beyond the amount needed to reorder the drug.

The example embodiments further solve the technical challenges of conventional software that fail to consider the financial impact in determining when to reorder a drug in combination with maintaining compliance with a drug discount program.

Thus, the example embodiments solve a number of technical challenges.

The computers and servers in FIG. 1 may be general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The computers and servers in FIG. 1 may be running on any one of many operating systems including, but not limited to WINDOWS, UNIX, LINUX, MAC OS, or Windows (XP, VISTA, etc.). It is contemplated, however, that any suitable operating system may be used for the present invention. The computers and servers in FIG. 1 may be a cluster of web servers, which may each be LINUX based and supported by a load balancer that decides which of the cluster of web servers should process a request based upon the current request-load of the available server(s).

The computers and servers in FIG. 1 are shown interconnected be lines. The lines may represent networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device depicted in FIG. 1 may communicate with any other device via one or more networks.

System 100 may include additional devices and networks beyond those shown. Further, the functionality described as being performed by one device may be distributed and performed by two or more devices. Multiple devices shown in FIG. 1 may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, systems and methods described herein may be configured to facilitate compliance with a drug discount program. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed is:

1. An analysis apparatus comprising:
   at least one processor; and
   at least one memory storing instructions that, when executed by the at least one processor, cause the apparatus at least to perform:
   receiving dispensation data corresponding to dispensation of a drug associated with a covered entity, wherein the dispensation data comprises a proprietary code of the covered entity for identifying the drug and a dispensed quantity of the drug;
   mapping the proprietary code included in the dispensation data to a standardized drug identification code for the drug;
   retrieving a first audit record based on the standardized drug identification code, wherein the first audit record identifies an order quantity of the drug ordered by the covered entity using first and second discount pricing accounts;
   allocating the dispensed quantity of the drug to the first audit record up to an amount that equals but does not exceed the order quantity;
   applying a reorder rule to determine when to reorder the drug, wherein the reorder rule indicates:
      reordering the drug for the first discount pricing account a predetermined amount of time after the drug has been dispensed above the order quantity required for the first audit record to be fully allocated, wherein the predetermined amount of time includes a function of an average rate that the drug is dispensed over time and the predetermined amount of time varies over time as the average rate changes, and
      modifying a threshold amount of the drug for reordering based on: 1) a first discount of the first discount pricing account in comparison to a second discount of the first discount pricing account, or 2) the first discount of the first discount pricing account in comparison to a non-discounted price of a non-discounted pricing account;
      wherein a higher first discount increases the threshold, and a lower first discount lowers the threshold;
   transferring a returned quantity of the drug from the first audit record to one or more of a plurality of second audit records after the predetermined amount of time such that at least the first audit record remains fully allocated;
   subsequent to determining to reorder the drug in response to applying the reorder rule and subsequent to transferring the returned quantity of the drug from the first audit record to one or more of the plurality of second audit records after the predetermined amount of time such that at least the first audit record remains fully allocated, communicating to a distributor an order message comprising the order quantity, a first audit record identifier, and the standardized drug identification code to reorder the drug using a 340B pricing account corresponding to the first audit record and for causing the distributor to ship the drug to a mailing address associated with the covered entity;
   allocating a remainder of the dispensed quantity of the drug to the one or more of the plurality of second audit records, the plurality of second audit records each including a second audit record identifier; and
   assigning one of the second audit record identifiers to the first audit record to automatically link a second audit record of the plurality of second audit records to the first audit record;
   wherein each of the plurality of second audit records indicates reordering of the drug using a non-340B pricing account during a predetermined amount of time, and the first audit record includes all audit record identifiers corresponding to the plurality of second audit records that result from reordering the drug to create a chain between audit records corresponding to a first time a drug was ordered through each time an audit record was generated when the drug was reordered.

2. A non-transitory computer readable medium storing computer executable instructions that, when executed, cause an apparatus at least to perform:
   receiving dispensation data corresponding to dispensation of a drug associated with a covered entity, wherein the dispensation data comprises a proprietary code of the covered entity for identifying the drug and a dispensed quantity of the drug;
   mapping the proprietary code included in the dispensation data to a standardized drug identification code for the drug;
   retrieving a first audit record based on the standardized drug identification code, wherein the first audit record identifies an order quantity of the drug ordered by the covered entity using first and second discount pricing accounts;
   allocating the dispensed quantity of the drug to the first audit record up to an amount that equals but does not exceed the order quantity;

applying a reorder rule to determine when to reorder the drug, wherein the reorder rule indicates:
  reordering the drug for the first discount pricing account a predetermined amount of time after the drug has been dispensed above the order quantity required for the first audit record to be fully allocated, wherein the predetermined amount of time includes a function of an average rate that the drug is dispensed over time and the predetermined amount of time varies over time as the average rate changes, and
  modifying a threshold amount of the drug for reordering based on: 1) a first discount of the first discount pricing account in comparison to a second discount of the first discount pricing account, or 2) the first discount of the first discount pricing account in comparison to a non-discounted price of a non-discounted pricing account;
  wherein a higher first discount increases the threshold, and a lower first discount lowers the threshold;
transferring a returned quantity of the drug from the first audit record to one or more of a plurality of second audit records after the predetermined amount of time such that at least the first audit record remains fully allocated;
subsequent to determining to reorder the drug in response to applying the reorder rule and subsequent to transferring the returned quantity of the drug from the first audit record to one or more of the plurality of second audit records after the predetermined amount of time such that at least the first audit record remains fully allocated, communicating to a distributor an order message comprising the order quantity, a first audit record identifier, and the standardized drug identification code to reorder the drug using the 340B pricing account corresponding to the first audit record and for causing the distributor to ship the drug to a mailing address associated with the covered entity;
allocating a remainder of the dispensed quantity of the drug to the one or more of the plurality of second audit records, the plurality of second audit records each including a second audit record identifier; and
assigning one of the second audit record identifiers to the first audit record to automatically link a second audit record of the plurality of second audit records to the first audit record;
wherein each of the plurality of second audit records indicates reordering of the drug using a non-340B pricing account during a predetermined amount of time, and the first audit record includes all audit record identifiers corresponding to the plurality of second audit records that result from reordering the drug to create a chain between audit records corresponding to a first time a drug was ordered through each time an audit record was generated when the drug was reordered.

3. A computer-implemented method comprising:
receiving dispensation data corresponding to dispensation of a drug associated with a covered entity, wherein the dispensation data comprises a proprietary code of the covered entity for identifying the drug and a dispensed quantity of the drug;
mapping the proprietary code included in the dispensation data to a standardized drug identification code for the drug;
retrieving a first audit record based on the standardized drug identification code, wherein the first audit record identifies an order quantity of the drug ordered by the covered entity using first and second discount pricing accounts;
allocating the dispensed quantity of the drug to the first audit record up to an amount that equals but does not exceed the order quantity;
applying a reorder rule to determine when to reorder the drug, wherein the reorder rule indicates:
  reordering the drug for the first discount pricing account a predetermined amount of time after the drug has been dispensed above the order quantity required for the first audit record to be fully allocated, wherein the predetermined amount of time includes a function of an average rate that the drug is dispensed over time and the predetermined amount of time varies over time as the average rate changes, and
  modifying a threshold amount of the drug for reordering based on: 1) a first discount of the first discount pricing account in comparison to a second discount of the first discount pricing account, or 2) the first discount of the first discount pricing account in comparison to a non-discounted price of a non-discounted pricing account;
  wherein a higher first discount increases the threshold, and a lower first discount lowers the threshold;
transferring a returned quantity of the drug from the first audit record to one or more of a plurality of second audit records after the predetermined amount of time such that at least the first audit record remains fully allocated;
subsequent to determining to reorder the drug in response to applying the reorder rule and subsequent to transferring the returned quantity of the drug from the first audit record to one or more of the plurality of second audit records after the predetermined amount of time such that at least the first audit record remains fully allocated, communicating to a distributor an order message comprising the order quantity, a first audit record identifier, and the standardized drug identification code to reorder the drug using the 340B pricing account corresponding to the first audit record and for causing the distributor to ship the drug to a mailing address associated with the covered entity;
allocating a remainder of the dispensed quantity of the drug to the one or more of the plurality of second audit records, the plurality of second audit records each including a second audit record identifier; and
assigning one of the second audit record identifiers to the first audit record to automatically link a second audit record of the plurality of second audit records to the first audit record;
wherein each of the plurality of second audit records indicates reordering of the drug using a non-340B pricing account during a predetermined amount of time, and the first audit record includes all audit record identifiers corresponding to the plurality of second audit records that result from reordering the drug to create a chain between audit records corresponding to a first time a drug was ordered through each time an audit record was generated when the drug was reordered.

* * * * *